United States Patent [19]

Umemura et al.

[11] Patent Number: 4,759,372

[45] Date of Patent: Jul. 26, 1988

[54] CONVEX ARRAY ULTRASONIC PROBE

[75] Inventors: Shinichiro Umemura; Hiroshi Ikeda, both of Hachiouji; Kageyoshi Katakura, Naka; Toshio Ogawa, Itsukaichi; Shinichi Kondo, Kodaira, all of Japan

[73] Assignees: Hitachi Medical Corp.; Hitachi Ltd., both of Tokyo, Japan

[21] Appl. No.: 916,791

[22] Filed: Oct. 8, 1986

[30] Foreign Application Priority Data

Oct. 9, 1985 [JP] Japan ................. 60-223608

[51] Int. Cl.⁴ ............................................. A61B 10/00
[52] U.S. Cl. .......................................... 128/660; 73/626
[58] Field of Search ............................ 120/660–661, 120/4; 73/618–620, 623, 626; 367/103; 310/369

[56] References Cited

U.S. PATENT DOCUMENTS

| | | | |
|---|---|---|---|
| 3,938,502 | 2/1976 | Bom | 128/661 X |
| 4,344,327 | 8/1982 | Yoshikawa et al. | 128/661 X |
| 4,409,982 | 10/1983 | Plesset et al. | 73/626 X |
| 4,605,009 | 8/1986 | Pourcelot et al. | 128/660 |

OTHER PUBLICATIONS

Hovelice, J. F. et al., "Medical Ultrasonic Imaging: An Overview", Proc. IEEE, vol. 67, No. 4, Apr. 1979.
Wells, P. N. T., "Biomedical Ultrasonics", Academic Press, London, 1977, pp. 244–245.

*Primary Examiner*—Francis J. Jaworski
*Attorney, Agent, or Firm*—Antonelli, Terry & Wands

[57] ABSTRACT

An ultrasonic probe used for ultrasonic diagnosis apparatus. A plurality of ultrasonic transducer elements are provided in a convexity at the tip of a probe so as to constitute a convex array ultrasonic probe. The curvature radius of the convexity is set at not greater than 12 mm and the pitch of adjacent transducer elements is set at not greater than 1/30 of the curvature radius and a ratio $\Delta/Y$ is set at not greater than 1/35, where Y represents the beam focal distance and $\Delta$ represents the lateral resolution of the probe.

6 Claims, 4 Drawing Sheets

CONVEX ARRAY ULTRASONIC PROBE

BACKGROUND OF THE INVENTION

The present invention relates to an ultrasonic probe used for ultrasonic diagnostic apparatus and the like.

Ultrasonic diagnostic apparatus are known which radiate ultrasonic pulse beams into an object to be examined, receiving the echoes which are reflected by the boundary of the structures of organs in accordance with a difference in acoustic impedance, displaying them on a display such as a cathode-ray tube, so that the structure of the organs can be observed from the displayed image. Since they enable the interior of the body to be diagnosed from the exterior, they are widely used.

An ultrasonic probe having an electroacoustic conversion element is used in order to transmit and receive ultrasonic waves. A driving signal of a desired frequency is supplied to the electroacoustic conversion element, whereby ultrasonic beams are radiated from the excited element and the reflected echo is converted into an electrical signal.

Especially, a convex array ultrasonic probe with a tip having a curvature radius of less than 12 mm is very useful for cardiac diagnosis. The probe having a tip of such a small diameter has good operability, because, it enables the tip to be positioned at a part between adjacent ribs for imaging a heart of a patient. In addition, since such a convex array ultrasonic probe has a wide view, it is also useful for abdominal diagnosis. As an example of the convex array ultrasonic probes having a comparatively small curvature radius, one which is described in pp 72 to 76 "Ultrasonics" March, 1972, is conventionally known. However, since the array pitch of the transducer elements in this probe is larger than the radius of the element, it is difficult for this type of probe to realize the lateral resolution and acoustic SN ratio of a high level which are at present required in the medical diagnosis. Incidentally, in the above-described example, the strip-like transducer elements are provided around the shaft of the probe, and the probe therefore has a little different structure from the probe of the present invention which is provided with the transducer elements at the tip thereof.

SUMMARY OF THE INVENTION

Accordingly, it is an object of the present invention to eliminate the above-described problems in the prior art and to provide an ultrasonic probe which has not only the aforementioned good operability of a convex array ultrasonic probe with a tip having a comparatively small curvature radius (hereinunder referred to as "the radius of a probe curvature") but also a lateral resolution and acoustic SN ratio of a high level which are required in the present and future medical diagnosis.

To achieve this aim, in an ultrasonic probe according to the present invention, the curvature radius of a plurality of transducer elements arrayed in a convexity is set at less than 12 mm, which value is suitable for cardiac diagnosis performed through a part between ribs, and the array pitch of the elements is set at a small value.

The above and other objects, features and advantages of the present invention will become clear from the following description of the preferred enbodiment thereof, taken in conjunction with the accompanying drawings.

DESCRIPTION OF THE PREFERRED EMBODIMENTS

The structure of the present invention will be explained hereinunder.

The array pitch of the elements of an ultrasonic probe, which is the main feature of the present invention, will first be explained with reference to FIG. 1.

Figure 1:
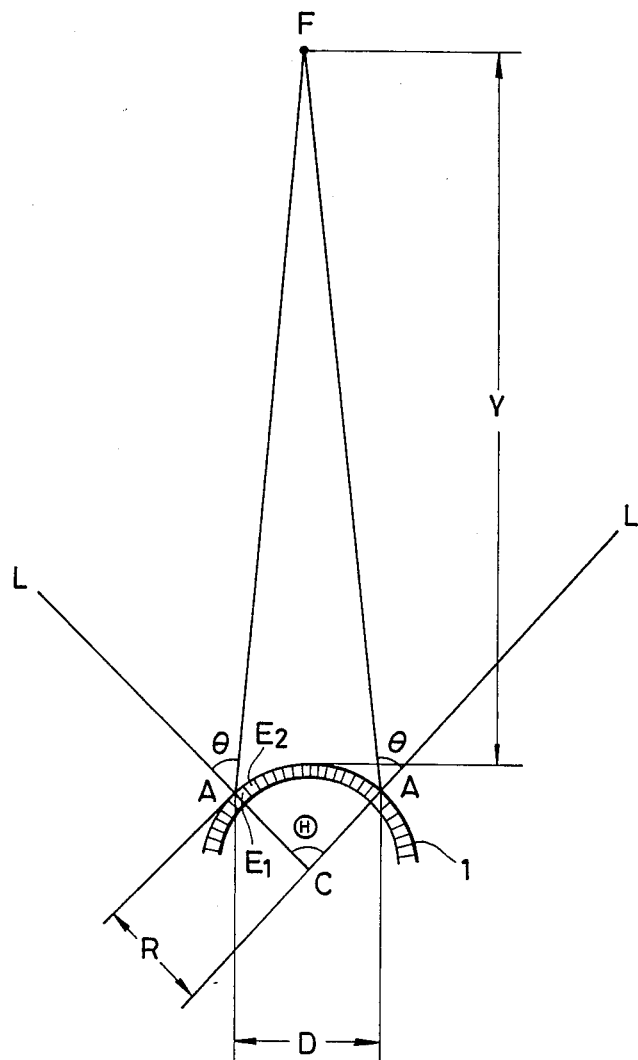
FIG. 1 shows a geometrical arrangement of the main part of an embodiment of a convex array ultrasonic probe according to the present invention, which explains the function of the probe in imaging a diagnostic picture.

The strip-like elements shown in FIG. 1 are provided in a semicircular configuration at the tip of the probe, and FIG. 1 shows the arrangement of each element as viewed from the top thereof.

The transmission and reception aperture D of the probe which is necessary for realizing the required lateral resolution is calculated. The relationship between the lateral resolution $\Delta$ of transmission and reception, which is defined as the half power beam width, the focal distance Y between the probe 1 and a focal point F, the wavelength $\lambda$ of an ultrasonic wave, and the aperture D is represented by the following formula:

$$D/\pi \approx (6/7) \cdot (y/\Delta), \tag{1}$$

For example, if the lateral resolution ($\Delta$) is approximately $\Delta \lesssim 2$ mm, which is required of a picture in the vicinity of the distance (Y) of 70 mm, this distance being often used in cardiac diagnosis, the necessary aperture D is obtained from the following formula:

$$D \gtrsim 30\lambda \tag{2}$$

The array pitch P which is necessary for realizing the required acoustic SN ratio is next calculated. In order to prevent the increase in the strength of the grating lobe which is the main factor for deteriorating the acoustic SN ratio in an electronic scanner for imaging, the array pitch P or physical spacing of the elements is determined in the following way in accordance with the sampling theory. That is, the array pitch P is so determined that when the ultrasonic wave transmitted from the probe 1 in FIG. 1 is reflected at the position of the focal point F and is received by the probe 1, the phase difference of the receiving signal is not greater than $\lambda/2$, between adjacent elements, e.g., an element $E_1$ and an element $E_2$. Since the phase difference of signals between adjacent elements becomes ordinarily its maximum at the end A of the aperture D, the above-described condition that the phase difference is not greater than $\lambda/2$ between adjacent elements is equivalent to the following condition:

$$P \sin \theta \leq \lambda/2 \quad (3)$$

wherein $\theta$ represents the angle between the vertical line AL at the point A on the curvature of the probe 1 and the straight line AF drawn as shown in FIG. 1.

When the radius R of the probe curvature is adequately small in comparison with the focal length, namely the distance Y of imaging, $\theta$ is approximately equal to half the center angle $\Theta$ of the aperture D, as represented by the following formula:

$$\theta \approx \Theta/2 \quad (4)$$

When the center angle $\Theta$ is not extremely large, the aperture D and $\sin \theta$ are respectively approximated by the following formula:

$$D \approx R\Theta \quad (5)$$

$$\sin \theta \approx \theta \quad (6)$$

The following formula is obtained from the formulae (4), (5) and (6):

$$\sin \theta \approx D/2R \quad (7)$$

In order to hold the formulae (1) and (3) simultaneously, the following condition must be satisfied which is obtained from the formulae (1), (3) and (7):

$$P \leq (7/6) \cdot (\Delta/Y) \cdot R \quad (8)$$

If the above-described lateral resolution $\Delta$ which is required of an image in the vicinity of the distance Y of imaging Y=70 mm which is often used in cardiac diagnosis, is $\Delta \lesssim 2$ mm, the following formula holds:

$$P \leq R/30 \quad (9)$$

In other words, it is necessary to set the array pitch P of the elements at not greater than $(7/6) \cdot (\Delta/y) \cdot R$ and, if Y=70 mm and $\Delta \lesssim 2$ mm, to set the array pitch P of the elements at not greater than 1/30 of the curvature radius R, in order to realize the required lateral resolution and acoustic SN ratio simultaneously by a convex array ultrasonic probe.

The present invention will be explained in more detail in the following with reference to an embodiment.

Figure 2:
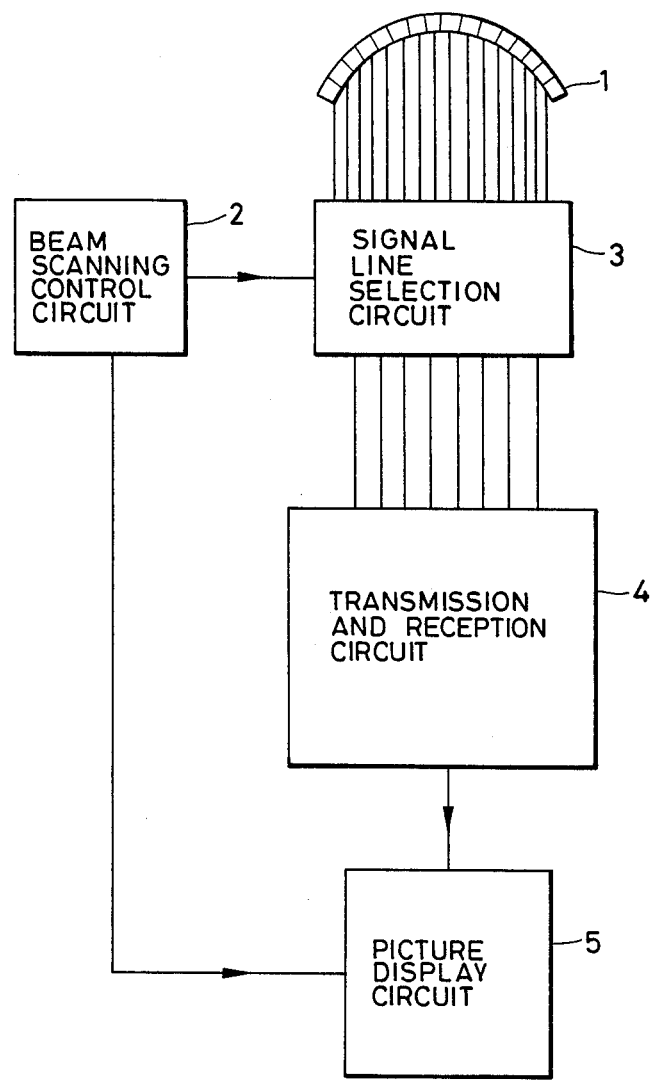
FIG. 2 is a block diagram of the structure of an ultrasonic imaging apparatus using the embodiment of a convex array ultrasonic probe.
Figure 3:
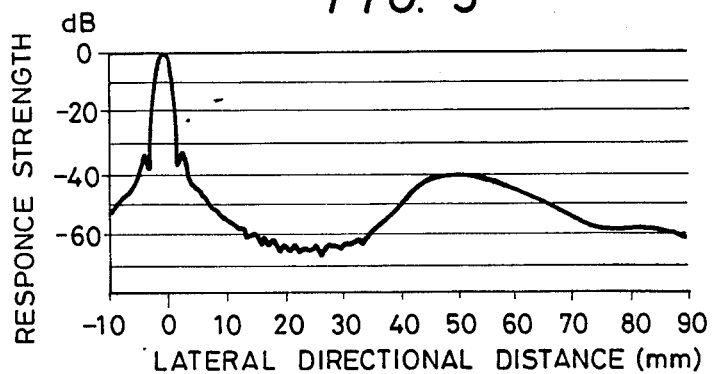
FIG. 3 is a graph of the logarithms of the directivity pattern obtained using the probe according to the present invention.

FIG. 3 shows an example of the directivity pattern obtained by an ultrasonic imaging apparatus in which the convex array ultrasonic probe of the present invention is used and which has the structure shown in the block diagram of FIG. 2. The ultrasonic probe in this example uses piezoelectric ceramic as an electroacoustic conversion material, and the central frequency of the ultrasonic wave used is 5.0 MHz and the radius R of the probe curvature is 10 mm. The directivity pattern is obtained by measuring the magnitude distribution of the reflected signal of a point reflector which is placed 70 mm distant from the probe 1 by scanning a transmission and reception beam in the lateral direction, and plotting the response strengths of the image. In FIG. 3, the ridge of the curve having a high peak of the response strength of the image and narrow width shows the main lobe which is at the (true) position of the point reflector, and a ridge which has a wide width shows a grating lobe. Since the pitch P of the elements in this example is set at 0.3 mm (<0.33 mm=R/30), the lateral resolution $\Delta$ reaches the practically necessary lateral resolution $\Delta$=2.0 mm (at a half power beam width of the main lobe), as is clear from FIG. 3, and the apparatus of this example has succeeded in realizing the practically necessary acoustic SN ratio of 40 dB (the ratio of strengths between the main lobe and the grating lobe). The aperture D for transmission and reception at this time is 10 mm.

Figure 4:
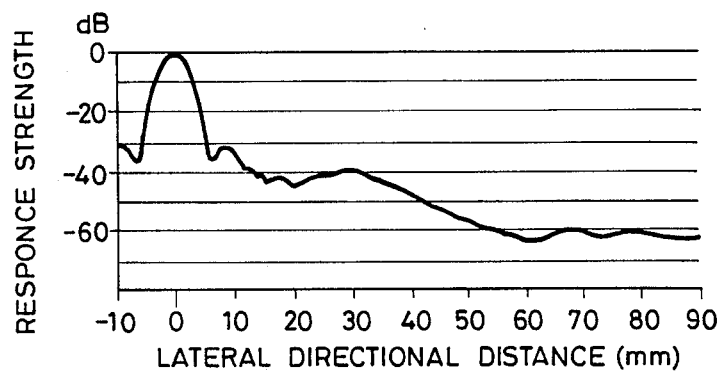
FIGS. 4 and 5 are graphs of the logarithms of the directivity pattern obtained when the present invention is not applied.
Figure 5:
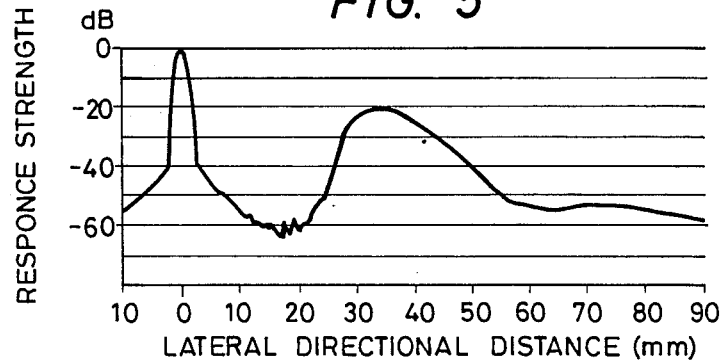

For comparison, the directivity patterns obtained in the case of setting the pitch P of the elements at 0.5 mm (>0.33 mm=R/30) without applying the present invention are shown in FIGS. 4 and 5. In this case, the aperture D is forced to be limited to 3.6 mm in order to realize the practically necessary acoustic SN ratio 40 dB. As a result, the directivity pattern is such as that shown in FIG. 4, and the lateral resolution $\Delta$ is disadvantageously more than 5 mm. On the other hand, in order to realize the practically necessary lateral resolution $\Delta$=2 mm, the directivity pattern is such as that shown in FIG. 5, and the acoustic SN ratio is disadvantageously about 20 dB. In other words, it is impossible to achieve both the practically necessary lateral resolution and the practically necessary acoustic SN ratio simultaneously without applying the present invention.

Figure 6:
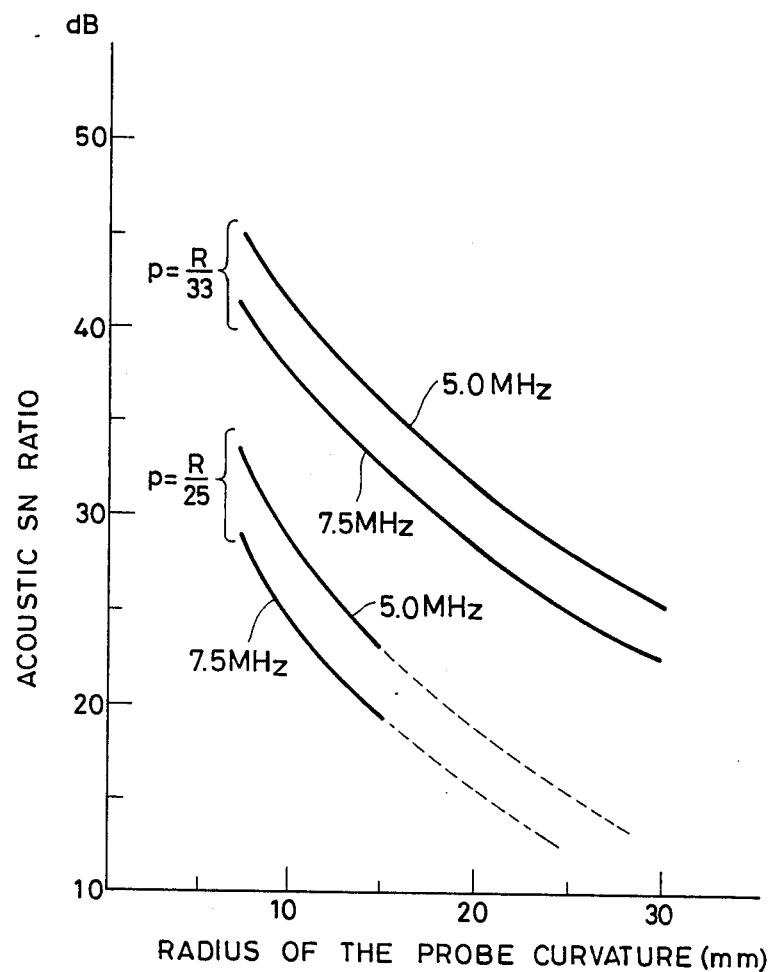
FIG. 6 is a characteristic diagram of the relative relationship between the radius of the probe curvature, the pitch of the elements and the acoustic SN ratio of an ultrasonic probe.

FIG. 6 shows the acoustic SN ratio obtained when a transmitting and receiving beam having a lateral resolution of 2 mm at a focal distance of 70 mm as a function of the radius of the probe curvature. The acoustic SN ratios in the cases in which the pitch of the elements is P=R/33 and P=R/25 are plotted and compared in relation to the frequencies of the ultrasonic waves of both 5.0 MHz and 7.7 MHz. The practically necessary acoustic SN ratio more than 40 dB is obtained when $R \lesssim 12$ mm in the case of the pitch of the elements P=R/33, while it is not obtained in the case of the pitch of the elements P=R/25. It will be understood that the necessary acoustic SN ratio is obtained only when the present invention is applied. This phenomenon is substantially the same even if the frequency of the ultrasonic wave is changed from 5.0 MHz to 7.5 MHz, namely, by 50%.

As described above, according to the present invention, a convex array ultrasonic probe having a comparatively small curvature radius enables such a high picture resolution as not greater than 2 mm at the half power beam width and such a high acoustic SN ratio as not smaller than 40 dB simultaneously as well as a high operability to be realized. Thus, the present invention is very effective in the industrial and medical fields.

While there has been described what is at present considered to be a preferred embodiment of the invention, it will be understood that various modifications may be made thereto, and it is intended that the appended claims cover all such modifications as fall within the scope of the invention.

What is claimed is:

1. In a convex array ultrasonic probe comprising a probe member having a tip and an ultrasonic transducer consisting of a plurality of ultrasonic wave transducer elements with a predetermined pitch aligned adjacent to each other along a convexity in a direction of transmission of an ultrasonic wave, the ultrasonic transducer being provided at the tip of said probe member, the improvement comprising the arrangement in which the curvature radius R of said convexity is set at not greater than 12 mm, and the predetermined pitch or physical spacing of adjacent transducer elements is set at not greater than $(7/6)\cdot(\Delta/Y)$ of said curvature radius R, wherein $\Delta$ represents the lateral resolution or half-power beam width of transmission and reception which is required of said ultrasonic probe in the vicinity of a focal point, and Y represents the distance between the probe and said focal point, the ratio of $\Delta/Y$ being set at not greater than 1/35.

2. A convex array ultrasonic probe according to claim 1, wherein said pitch of adjacent transducer elements is set at less than 1/30 of said curvature radius R.

3. A convex array ultrasonic probe comprising:
a probe member; and
an ultrasonic transducer for transmitting an ultrasonic beam in a direction and receiving said ultrasonic beam, said ultrasonic transducer consisting of a plurality of ultrasonic wave transducer elements at a tip of said probe member and aligned adjacent to each other with a predetermined pitch or physical spacing along a convexity in the direction of transmission for the ultrasonic beam, the convexity of said ultrasonic transducer having a radius of curvature R no greater than 12 mm, the ultrasonic probe having a characterizing beam ratio $\Delta/Y$ which is no greater than 1/35, wherein Y represents beam focal distance from the probe and $\Delta$ represents the lateral resolution or half-power beam width of the beam for transmission and reception in the vicinity of said focal distance, the predetermined pitch of adjacent transducer elements being no greater than $(7/6)\cdot(\Delta/Y)$ of said radius of curvature R.

4. A convex array ultrasonic probe according to claim 3, wherein said beam focal distance Y is no greater than 70 mm.

5. A convex array ultrasonic probe according to claim 3, wherein said lateral resolution $\Delta$ is in the direction of the ultrasonic beam transmission.

6. A convex array ultrasonic probe according to claim 3, wherein said beam focal distance Y is no greater than 70 mm and said lateral resolution $\Delta$ is in the direction of the ultrasonic beam transmission.

* * * * *